United States Patent [19]

Chevallier et al.

[11] 4,107,079
[45] Aug. 15, 1978

[54] INSOLUBLE METALLIC COMPLEXES AND CATALYSTS THEREFROM

[75] Inventors: Yvonick Chevallier, Decines; Jacques-Pierre Martinaud, Lyon; François Meiller, Palaiseau; Jean Berthoux, Decines, all of France

[73] Assignee: Rhone-Poulenc Industries, Paris, France

[21] Appl. No.: 762,474

[22] Filed: Jan. 26, 1977

Related U.S. Application Data

[63] Continuation-in-part of Ser. No. 504,710, Sep. 10, 1974, abandoned.

[30] Foreign Application Priority Data

Sep. 10, 1973 [FR] France ................................. 73 33006

[51] Int. Cl.$^2$ ..................... B01J 23/42; B01J 23/44; B01J 23/46; B01J 27/10
[52] U.S. Cl. ............................. 252/429 R; 252/428; 252/430; 252/431 C; 252/431 N; 260/583 R; 260/583 M; 260/604 HF; 260/683.9; 568/909
[58] Field of Search .................. 252/429 R, 430, 428, 252/431 C, 431 N, 431 P

[56] References Cited

U.S. PATENT DOCUMENTS

| | | | |
|---|---|---|---|
| 3,389,092 | 6/1968 | Sanford et al. | 252/430 |
| 3,487,112 | 12/1969 | Paulik et al. | 252/429 R |
| 3,511,880 | 5/1970 | Booth | 252/429 R X |
| 3,536,692 | 10/1970 | Otsuka et al. | 252/429 R X |
| 3,646,115 | 2/1972 | Starr | 252/429 R X |
| 3,829,392 | 8/1974 | Wulff | 252/430 |
| 3,839,385 | 10/1974 | Meiller et al. | 252/430 X |

*Primary Examiner*—Patrick P. Garvin

[57] ABSTRACT

Solid catalyst, insoluble in organic and aqueous solvents and having the general formula:

$$A - M (L')_n (L'')_q$$

in which A is an insoluble ligand, M is a Group VIII noble metal, L' and L'' are ligands and n and q are intergers of 0 to 6 are provided for the advantageous catalysis of hydroformylation, and hydrogenation of olefins and the preparation of tertiary amines from olefins.

14 Claims, No Drawings

INSOLUBLE METALLIC COMPLEXES AND CATALYSTS THEREFROM

CROSS-REFERENCE TO RELATED APPLICATION

This application is a continuation-in-part of application Ser. No. 504,710, filed Sept. 10, 1974, now abandoned.

BACKGROUND OF THE INVENTION

1. Field of the Invention

The present invention relates to new insoluble metallic complexes and to their use as catalysts in various reactions such as hydroformylation, hydrogenation and the preparation of tertiary amines by the reaction of an olefin, carbon monoxide and hydrogen with a secondary amine.

2. Description of the Prior Art

Generally, the catalysts employed in such reactions are soluble catalysts derived from Group VIII noble metals which are difficult to recover because the active catalyst is present in the form of coordination complexes which are dissolved in the reaction medium.

Insoluble catalysts forming heterogeneous catalyst-reaction medium systems and obtained from soluble complexes of noble metals have heretofore been used in various reactions. For example, insoluble ligands prepared from organic polymers with particular functional groups thereon, such as amines, phosphines (French Pat. No. 1,583,037, filed Oct. 1, 1968) and vinylpyridine (U.S. Pat. No. 3,636,159, filed Dec. 19, 1968) have been proposed. Likewise, inorganic compounds into which a phosphor-containing radical has been introduced, either on silica or alumina (British Pat. No. 1,275,733) or an alkoxysilane having a phosphine group thereon or a metallic complex of this alkoxysilane with silica (French patent application Ser. No. 70/45 824, now French Pat. No. 2,071,942, filed Dec. 18, 1970), have been suggested for the hydroformylation of ethylenically unsaturated hydrocarbons to yield aldehydes and alcohols (French patent application Ser. No. 70/45 607, now French Pat. No. 2,073,940, filed Dec. 17, 1970).

The advantage of such catalysts is that the precious, relatively expensive metals therein remain complexed and are not released into the effluent of the reactor and are easily recovered therefrom in their original catalytically active form.

The capacity of these solid catalysts to retain the metal after reaction is due to the coordinating element of the insoluble ligand and not to other coordinating elements ultimately associated with the metal but not directly linked to the insoluble ligand.

Up to the present time, in such catalysts, phosphorus was generally used as a donor heteroatom, and was linked to an inorganic or organic, polymeric matrix. Although these catalysts display satisfactory catalytic activity, the metal retention properties of same have rendered such catalysts economically unsuitable for commercial applications.

SUMMARY OF THE INVENTION

The present invention relates to solid catalysts, insoluble in organic solvents and water, which are of the metallic complex type and comprise an insoluble ligand, a noble metal of Group VIII and other ligands linked to this noble metal and having the following general formula:

$$A - M (L')_n (L'')_q$$

wherein A is an insoluble ligand prepared by reacting an alkoxysilane or a chlorosilane which contains an amine radical or a carboxylic acid radical with silica or alumina or by reacting a vinylalkoxysilane or a vinylchlorosilane and then copolymerizing the resultant product with vinylpyridine; M is a noble metal of Group VIII; L' and L'' are identical or different ligands such as chlorine, carbon monoxide, olefins, and hydrocarbyl substituted amines, phosphines, phophites and arsines; and $n$ and $q$ are integers between about 0 and 6.

It is, therefore, a primary object of the present invention to provide insoluble metallic complexes which display a high degree of catalytic activity of olefin conversion reactions.

A further object of the instant invention is to provide catalytically active metallic complexes wherein the metal thereof remains complexed with the coordinating element of an insoluble ligand and is not released into the effluent from the reactor.

Still another object of the invention is the preparation of a catalytic insoluble metallic complex suitable for the catalysis of olefin conversion to aldehydes, alcohols and tertiary amines which complex may be recycled and reused in subsequent reactions without any noticeable reduction in the catalytic activity of the recycled complex.

Other objects, features and advantages of this invention will become more apparent to those skilled in the art from the detailed description of the preferred embodiments which follows.

DETAILED DESCRIPTION OF THE PREFERRED EMBODIMENTS

The catalysts of the present invention have a high metal retention capacity which significantly enhances the economic feasability of utilizing same on a commercial scale.

The catalysts of the present invention may be prepared and isolated by either of the two following methods: First, by the reaction of a salt or a coordination complex of a noble metal of Group VIII with an insoluble ligand such as described hereinabove. The noble metals of Group VIII are ruthenium, rhodium, palladium, osmium, iridium and platinum. The insoluble ligands may be obtained, for example, by reacting silica or alumina with an alkoxysilane or chlorosilane having from 1 to 20 carbon atoms and having a radical comprising an amine or carboxylic acid function.

The radical comprising an amine function is derived from a primary, secondary or tertiary mono-amine or polyamine. Their substituents have from 1 to 20 carbon atoms and are selected from the group consisting of alkyl, cycloalkyl, aryl, aryloxy, aralkyl and alkaryl radicals. Suitable radicals are: (amino 2 ethyl)amino, aminophenoxy, methylaminophenoxy, dimethylaminophenoxy, aminophenyl, methylaminophenyl, dimethylaminophenyl, phenylaminophenyl, diphenylaminophenyl, methylphenylaminophenyl, methylamino-, ethylamino-, dimethylamino-, diethylamino-, anilino-, diphenylamino-, methylphenylamino-, (dimethylamino 2)ethyl, cyclohexylamino-, methylaminocyclohexyl-, dimethylaminocyclohexyl, aminocyclohexyl, piperidyl, methylpiperidyl, pyridil, pyridyl 2 ethyl, pycolyl.

The radical comprising a carboxylic acid function hat from 1 to 20 carbon atoms and is selected from the group consisting of alkylcarboxylic, alkenylcarboxylic, arylcarboxylic, alkaryl carboxylic and aralkyl carboxylic radicals. Suitable radicals are:

phenylcarboxylic: — $C_6H_4$ — COOH
acrylic: — CH=CH — COOH
acetic: — $CH_2$ — COOH
propionic: — $CH_2$ — $CH_2$ — COOH
toluic: — $CH_2$ — $C_6H_4$ — COOH New compounds such as those described in commonly owned French Patent Application No. 73/25 698, now French Patent No. 2,236,552 filed July 13, 1973, corresponding to U.S. Pat. No. 3,969,261, are also useful. These compounds are anionic ion exchangers on mineral substrates and consisting of organic groups grafted by means of silicon atoms onto inorganic porous substrates having hydroxyl groups at their surfaces. The organic groups comprise one or more silicon atoms and aminated functions separated from silicon atoms by organic groups including at least three carbon atoms.

Compounds described in commonly owned French patent application No. 73/29 950, now French Pat. No. 2,245,663 filed Aug. 17, 1973, corresponding to U.S. Pat. No. 4,049,691, may also be used. These are aromatic, aminated silanes, the formula of which is as follows:

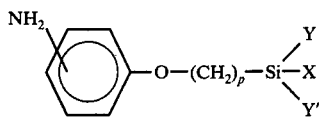

wherein $p$ is an integer between about 2 and 4, X is a linear or branched chain alkoxy group having 1 to 8 carbon atoms; Y and Y' may be identical or different and represent a methyl, ethyl or phenyl group, or a linear or branched chain alkoxy group of about 1 to 8 carbon atoms. Dimers and linear or cross-linked polymers of such silanes may, likewise, be utilized.

Ligands represented by L' and L" in the general formula are the same or different and can be chlorine, carbon monoxide, olefins and hydrocarbyl substituted amines, phosphines, phosphites and arsines represented by the formulas:

R'R"R''' N (R'O) (R"O) (R''' O) P

R'R"R''' P R'R"R''' As wherein R'R"R''' identical or different are H or hydrocarbyl moieties having from 1 to 20 carbon atoms selected from the group consisting of alkyl, cycloalkyl, aryl, aralkyl and alkaryl.

Suitable ligands which may be used in accordance with this invention include: trimethylphosphine, triethylphosphine, tributylphosphine, triphenylphosphine, phenyldimethylphosphine, methyldiethylphosphine, bis diphenylphosphinoethane, tricyclohexylphosphine, trimethylphosphite, tributylphosphite, triphenylphosphite, trinonylphenylphosphite, tricyclohexylphosphite, phosphite de trimethylolpropane, trimethylamine, tributylamine, triphenylamine, phenyldethylamine, toluidine, aniline, methylamine, dimethylamine, ethylamine, cyclohexylamine, cyclohexylamine, phenylethylamine, triphenylarsine, triethylarsine, ethylene, cyclooctene, cyclooctadiene, norbornadiene.

Alternatively, the insoluble ligand may be obtained by reacting a vinylalkoxysilane or a vinylchlorosilane with silica or alumina, and then copolymerizing the resultant product with vinylpyridine or acrylic acid, according to known methods.

The second method of preparing the insoluble catalysts of the present invention is by the reaction of a salt or a coordination complex of a noble metal of Group VIII with a chlorosilane or an alkoxysilane having an amine or carboxylic acid function in order to obtain a different coordination complex which is then reacted, in a second step, with an inorganic solid compound containing hydroxyl groups, such as silica or alumina. The catalyst may be used after isolation or prepared "in situ", by introducing the insoluble ligand and the salt or metallic complex simultaneously into the reactor.

When the salt or metallic complex used for the preparation of the catalyst does not comprise ligand containing trivalent phosphorus or arsenic such as phosphines, phosphites or arsines, the addition of such a ligand may be advantageous in order to increase the catalytic activity of the system, if necessary. The phosphorus or arsenic so added is not part of the insoluble ligand.

The following non-limitative examples are illustrative of the present invention.

First, examples of the preparation of ligands such as those described hereinabove will be given followed by exemplary reactions of these ligands with a salt or a coordination complex of a noble metal of Group VIII.

Preparation of Ligand A

Into 500 ml xylene are introduced 500 g balls of silica gel (specific area 415 m²/g) previously dried under reduced pressure at 150° C., for 4 hours and 100 g of the silane

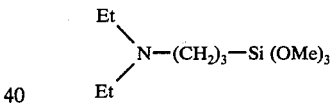

The mixture is heated under stirring, at 190° C. for 8 hours, and is filtered. After washing with acetone and drying under reduced pressure at 120° C. for 4 hours, the solid product obtained contains 7% of carbon, 1% of nitrogen and the degree of exchange is 0.4 meq./g.

Preparation of Ligand B

The procedure used for ligand A is repeated, except 500 g balls of silica gel and 100 g of the silane

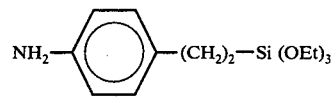

are introduced. The product obtained contains 0.8% of nitrogen.

Preparation of Ligand C

The procedure used for ligand A is repeated except 500 g balls of silica gel and 100 g of the silane

are introduced. The product obtained contains 2% of nitrogen.

Preparation of Ligands D, E, F

These ligands were prepared according to the method of F. Runge et al., *Macromolecular Chem.*, 1965, 81, p. 68.

Ligand D

Vinyltrichlorosilane is reacted with balls of silica gel (specific area 400 m²/g). The product obtained is copolymerized with 4-vinylpyridine. The resulting product contains 1.6% of nitrogen.

Ligand E

The procedure used for ligand D is repeated except alumina is used instead of silica. The product obtained contains 0.7% of nitrogen.

Ligand F

Vinyltrichlorosilane is reacted with balls of silica gel (specific area 400 m²/g). The product obtained is then copolymerized with acrylic acid.

The examples hereinbelow further describe the preparation of catalysts according to the invention utilizing the above ligands as starting materials.

All of the preparations are carried out under nitrogen free of oxygen, and the solvents were dried on molecular sieves and degased with nitrogen.

EXAMPLE 1

37.8 mg of $Rh_2Cl_2(CO)_4$ [dichlorotetracarbonyldirhodium] are introduced into a suspension of 2 g of ligand A in 20 ml of toluene. The mixture is stirred for a few minutes at room temperature, then for one hour at 50° C. A brown solid is obtained by decantation, washed with toluene, hexane and dried under reduced pressure for 24 hours. The complex contains 1% by weight of rhodium.

EXAMPLE 2

180 mg of $RhCl(PPh)_3$ [tris (triphenylphosphine) chlororhodium] are introduced into a suspension of 2 g of ligand A in 20 ml of toluene. The mixture is stirred for 10 minutes at room temperature, then for 2 hours at 80° C. A liquid, slightly yellow-colored phase is obtained by decantation, and a solid product which is washed three times with 10 ml of toluene at 80° C., then with 10 ml of hexane is also obtained. After drying under reduced pressure for 24 hours at room temperature, the resultant complex obtained contains 0.8% of rhodium.

EXAMPLE 3

52 mg of hydrated ruthenium trichloride containing 20 g of ruthenium are introduced into a suspension of 2 g of ligand A in 20 ml of ethanol. The mixture is stirred at room temperature for 10 minutes, then for 1 hour and 30 minutes at 80° C. A solid product and a liquid colorless phase are obtained by decantation. The solid product is washed three times with ethanol and dried under reduced pressure at room temperature for 24 hours. The solid compound obtained contains 1% by weight of ruthenium.

EXAMPLE 4

A catalyst containing 0.1% of Rh is prepared by the reaction of 4.1 mg of $Rh_2Cl_2(CO)_4$ with 2.2 g of ligand B. The isolation procedure of Example 1 is repeated.

EXAMPLE 5

A catalyst containing 0.93% of Rh is prepared by the reaction of 29.3 mg of $RhCl(CO)_2$p-toluidine [paratoluidine dicarbonylchlororhodium] with 1 g of ligand B. The recovery procedure of Example 2 is repeated.

EXAMPLE 6

A catalyst containing 1% of Rh is prepared by the reaction of 38 mg of $Rh_2Cl_2(CO)_4$ with 2 g of ligand C. The recovery procedure of Example 1 is repeated.

EXAMPLE 7

A solid catalyst containing 1% of Rh is prepared by reaction of 38 mg of $Rh_2Cl_2(CO)_4$ with 2 g of ligand D. The isolation procedure of Example 2 is followed.

EXAMPLE 8

A solid catalyst containing 1% of Rh is prepared by the reaction of 70 mg of $Rh_2Cl_2(C_8H_{14})_4$ [tetracyclooctenedichlorodirhodium] with 2 g of ligand D. The recovery procedure of Example 2 is repeated.

EXAMPLE 9

70 mg of $Rh_2Cl_2(C_8H_{14})_4$ are introduced into a suspension of 2 g of ligand D. The mixture is heated at 80° C., under stirring, for 15 minutes, then 54 mg of triphenylphosphine ($PPh_3$) in 29 ml of toluene are added. The stirring is continued at 80° C. for 2 hours. A liquid colorless phase is obtained by decantation along with a solid product which is washed with toluene, then hexane. After drying under reduced pressure for 24 hours, at room temperature, a solid, yellow-colored product is obtained containing 0.93% of Rh.

EXAMPLE 10

A catalyst prepared as described in Example 8, 265 mg is introduced into 5 ml of toluene to form a suspension. Then 8.1 mg of $P(OPh)_3$ in 10 ml of toluene are added to this suspension with stirring. The mixture is heated at 80° C. for 1 hour and 30 minutes and the solid obtained by decantation is washed with warm toluene (2 × 10 ml) then with hexane and dried under vacuum. The catalyst so prepared contains 1% of rhodium.

EXAMPLE 11

A catalyst containing 0.125% of Rh is prepared by reacting 39.5 mg of $Rh_2Cl_2(CO)_4$ with 1.990 g of ligand E. The purification procedure of Example 2 is repeated.

EXAMPLE 12

A catalyst containing 0.4% of platinum is prepared by the reaction of 148 mg of $Pt[P(OPh)_3]_4$ [tetrakis triphenylphosphite platinum] with 2 g of ligand E. The recovery procedure of Example 2 is repeated.

EXAMPLE 13

A catalyst containing 0.1% of Rh is prepared by the reaction of 7.7 mg of $Rh_2Cl_2(C_8H_{14})_4$ with 2.2 g of ligand F. The isolation procedure of Example 2 is repeated.

EXAMPLE 14

A catalyst containing 0.3% of Rh is prepared by reacting 39.8 mg of $Rh_2Cl_2(CO)_4$ with 2 g of ligand F. The purification procedure of Example 2 is repeated.

EXAMPLE 15

A catalyst containing 0.63% of palladium is prepared by reacting 73 mg of $PdCl_2(PhCN)_2$ [bis-benzonitriledichloropalladium] with 2 g of ligand F. The recovery procedure of Example 2 is repeated.

EXAMPLE 16

28 mg of soluble ligand

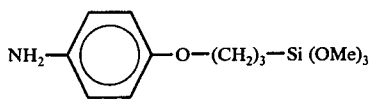

are introduced into a solution of 18.9 mg of $Rh_2Cl_2(CO)_4$ in 10 ml of xylene. The mixture is stirred for one hour at 50° C. The obtained solution is then added to a suspension of 1 g of silica (specific area 400 m²/g) in 10 ml of toluene. The stirring is continued for 4 hours at 80° C. A solid product is obtained by decantation, and washed with toluene, then hexane. After drying under reduced pressure, the isolated product contains 1% of Rh.

EXAMPLE 17

A catalyst containing 1% of Rh is prepared by the reaction of 100 mg of $RhCl_3(Py)_3$ [tripyridinetrichlororhodium] with 2 g of ligand D. The recovery procedure of Example 3 is repeated.

UTILITY

The catalyst of the instant invention are particularly effective in the following reactions:
— hydroformylation of olefins to aldehydes and alcohols with a conversion rate between 30 and 99%.
— preparation of tertiary amines from olefins with considerable selectivity in favor of amines (70 to 98% relative to consumed olefin)
— hydrogenation of olefins to form higher alkanes with conversion rates from about 40% to 95% and of nitro-compounds to form corresponding higher amines with a conversion rate approaching 90%.

The present catalysts are also active under moderated pressure conditions. Consequently, hydroformylation may be effectuated at under 10 to 120 bars (preferably from 20 to 90 bars) with solvents such as ketones, alcohols, ethers and hydrocarbons, particularly saturated hydrocarbons. Similarly, the preparation of tertiary amines may be carried out under 30 to 120 bars (preferably from 60 to 120 bars) with solvents such as alcohols, ethers and hydrocarbons, particularly saturated hydrocarbons. Likewise, the hydrogenation of olefins may be conducted from about 1 to 100 bars and preferably from 20 to 50 bars with the same solvents.

The reaction temperature of the various catalytic reactions are generally below 220° C. and preferably between about 100° and 200° C.

The use of coordinate complexes or ligands of noble metals results in a significant reduction in the concentration of metal present in the liquid effluent at the end of the reaction (on the order of ppm with respect to the product which is obtained in the case of hydroformylation or hydrogenation). This is one of the important improvements resulting from the utilization of the insoluble noble metal complexes of the invention.

The following examples further illustrate the use of the catalysts according to the invention in the aforementioned reactions.

EXAMPLES 18–30

Hydroformylation Reactions 10 ml of olefin, 10 ml of solvent and 200 mg of catalysts are introduced into a reactor equipped with gas injection, stirring and heating devices. Carbon monoxide and hydrogen are then injected at stated partial pressures. The mixture is then heated to the desired temperature and maintained for 5 hours with stirring. After cooling and pressure release the catalyst is separated by decantation. Then, the liquid phase is analyzed by vapor phase chromatography and the amount of olefin consumed, and the amounts of aldehydes and alcohols formed are determined. The concentration of metal in the reactive effluent is determined by flame emission spectrophotometry.

The results are set forth in Table I hereinbelow.

TABLE I (Hydroformylation)

| Example | Olefin | Catalyst | Solvent | H₂ (bars) | CO (bars) | T° C | Conversion rate of the olefin into aldehyde | Conversion rate of the olefin into alcohol | Metal concentration of the liquid phase effluent in ppm |
|---|---|---|---|---|---|---|---|---|---|
| 18 | 1-Octene | Example 1 | Toluene | 45 | 45 | 150 | 77 | — | 3.5 |
| 19 | 3-Pentene | Example 2 | Heptane | 20 | 20 | 150 | 64 | — | 4.0 |
| 20 | 1-Hexene | Example 7 | Heptane | 45 | 45 | 150 | 89 | 7 | 0.5 |
| 21 | 1-Decene | 200 mg ligand D + 4 mg Rh₂Cl₂(CO)₄ | Toluene | 45 | 45 | 150 | 87 (85) | 10 (5) | 4 (3) |
| 22 | 1-Hexene | Example 8 | Toluene | 20 | 20 | 150 | 32 | — | < 0.5 |
| 23 | 1-Hexene | Example 9 | Toluene | 20 | 20 | 150 | 56 (56) | — | 0.8 (<0.5) |
| 24 | 1-Hexene | Example 10 | Toluene | 20 | 20 | 150 | 66 | — | 2.5 |
| 25 | 1-Hexene | Example 9 +5.7 mg (OPh)₃ | Toluene | 20 | 20 | 150 | 86 | — | 2.7 |
| 26 | 1-Hexene | Example 1 | Toluene | 45 | 45 | 100 | 51 | — | 7.5 |
| 27 | 1-Hexene | Example 12 | Heptane | 45 | 45 | 150 | 30 | — | < 2.0 |
| 28 | 1-Hexene | Example 13 | Toluene | 45 | 45 | 150 | 52 (84) | 25 (—) |  |
| 29 | 1-Hexene | Example 11 | Toluene | 45 | 45 | 150 | 75 (87) | 14 (10) |  |
| 30 | 1-Hexene | Example 16 | Toluene | 45 | 45 | 150 | 79 |  |  |

The numbers in parentheses pertain to tests which were carried out with the catalyst recovered after the initial reaction. The reactor was brought to room temperature after completion of the reaction in Examples 19, 20 and 27. For the other examples, the reactor was cooled to −80° C. (at the end of the reaction). Example 28 contained 2,000 mg of catalyst.

EXAMPLES 31-36

Preparation of Tertiary Amines 6.7 g of olefin, 10 ml of solvent, 3.6 g of dimethylamine and a given weight of catalyst are introduced into a reactor. The mixture is then heated at 150° C. for 2 hours (or for 5 hours as described in Example 32). After completion of the reaction, the apparatus is cooled in a bath of acetonecarbonic acid before releasing the pressure. The amounts of amines formed are determined by vapor phase chromatography.

The results are given in Table II hereinbelow.

TABLE II (Tertiary Amines)

| Example | Olefin | Catalyst Example | Weight | $H_2$ (bars) | CO (bars) | Solvent | α | S | [M] |
|---|---|---|---|---|---|---|---|---|---|
| 31 | 1-Hexene | 1 | 200 mg | 60 | 60 | Toluene | 100 | 95 | 15 |
| 32 | 1-Decene | 3 | 200 mg | 90 | 30 | Ethanol | 75 | 77 | — |
| 33 | 1-Hexene | 4 | 2,000 mg | 60 | 60 | Toluene | 98 | 97 | 7 |
| 34 | 1-Dodecene | 5 | 220 mg | 60 | 60 | Toluene | 98 | 98 | 20 |
| 35 | 1-Hexene | 6 | 200 mg | 60 | 60 | Toluene | 100 | 96 | 28 |
| 36 | 1-Hexene | 14 | 670 mg | 60 | 60 | Toluene | 97 | 75 | — |

α = Conversion rate of olefin
S = Selectivity toward tertiary amines relative to consumed olefin
[M] = Metal concentration in the liquid phase effluent after reaction, expressed in ppm. The amount of catalyst used corresponds to 2 mg of metal

EXAMPLES 37-42

Hydrogenation Reactions

Hydrogenation reactions can be carried out using various starting materials such as linear, branched or cyclic olefins and aliphatic or aromatic nitro-compounds.

The starting material, solvent and catalyst are introduced into a reactor and hydrogen is injected under the desired pressure. The mixture is heated to the desired temperature for the desired reaction time.

The results are given in Table III hereinbelow.

TABLE III (Hydrogenation)

| Example | Catalyst Example | Weight | Unsaturated Starting Material | Solvent | $H_2$ (bars) | Duration of Reaction | Product Obtained (1) | [M] (2) |
|---|---|---|---|---|---|---|---|---|
| 37 | 1 | 800 mg | 1-Hexene (40 ml) | Toluene (40 ml) | 20 | 3 h 40' | Hexane - 94% | 0.5 ppm Rh |
| 38 | 1 | 800 mg | Nitrobenzene (40 ml) | Toluene (40 ml) | 20 | 7 h | Aniline - 96% | 0.5 ppm Rh |
| 39 | 3 | 200 mg | 1-Octene (10 ml) | Heptane (10 ml) | 20 | 3 h | Octane - 74% | 3 ppm Ru |
| 40 | 8 | 800 mg | 1-Hexene (40 ml) | Toluene (40 ml) | 20 | 3 h | Hexane - 94% | 0.5 ppm Rh |
| 41 | 12 | 500 mg | 1-Hexene (10 ml) | Heptane (10 ml) | 20−40+ | 4 h 1 h 30 | Hexane - 38% | < 2 ppm Pt |
| 42 | 15 | 312 mg | 1-Decene (10 ml) | Heptane (10 ml) | 20 | 5 h | Decane - 66% | < 1 ppm Pd |

All the tests were carried out at 100° C. At the end of the reaction, the reactor is cooled to room temperature (Examples 39, 41, 42) or to −80° C. (Examples 37, 38, 40).
(1) Conversion rate of unsaturated compound to hydrogenated product
(2) [M] = Metal concentration in the liquid phase after reaction The catalysts used in the various reactions described hereinabove are easily recovered and may be used repeatedly without loss of catalytic activity. For instance, a hydroformylation reaction was carried out with the catalyst of Example 8 with recovery of the catalyst and subsequently 20 hydroformylation reactions were conducted with the same recycled catalyst.

Thus, there is provided by the present invention catalytically active insoluble metallic complexes having an insoluble ligand moiety coordinately complexed with a Group VIII noble metal which are extremely valuable for the catalysis of hydroformylation and hydrogenation reactions and the preparation of tertiary amines from olefins and wherein the noble metal of the complex remains in complexed form to substantially prevent any loss of the metal in the reactor effluent or any reduction in the catalytic activity of the complex upon completion of the reaction whereby the metallic insoluble catalyst complex may be recovered and utilized in subsequent reactions.

While the invention has been described and illustrated with reference to certain preferred embodiments thereof, those skilled in the art will appreciate that various changes, modifications and substitutions therein can be made without departing from the spirit of the invention. It is intended, therefore, that the invention be limited only by the scope of the claims which follow.

What is claimed is:

1. A solid, solvent insoluble catalyst comprising a coordination complex of an insoluble ligand, a Group VIII noble metal and ligands other than said insoluble ligand bonded to said transition metal and having the formula:

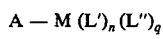

$$A - M (L')_n (L'')_q$$

wherein A is an insoluble ligand prepared by reacting an alkoxysilane or a chlorosilane which contains an amine radical or a carboxylic acid radical with silica or alumina or by reacting a vinylalkoxysilane or a vinylchlorosilane with silica or alumina and the copolymerizing the resultant product with vinylpyridine or acrylic acid; M is a Group VIII noble metal; L' and L'' are the same or different and comprise ligands selected from the group consisting of chlorine, carbon monoxide, olefins, hydrocarbyl substituted amines, phosphines, phosphites and arsines wherein any hydrocarbyl moiety has from 1 to 20 carbon atoms selected from the group consisting of alkyl, cycloalkyl, aryl, aralkyl and alkaryl; and n and q are integers between about 0 and 6.

2. The catalyst as defined by claim 1, wherein the insoluble ligand A comprises the product obtained by the reaction of silica and the silane

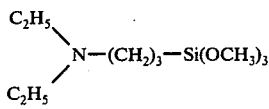

3. The catalyst as defined by claim 1, wherein the insoluble ligand A comprises the product obtained by the reaction of silica and the silane

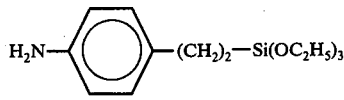

4. The catalyst as defined by claim 1, wherein the insoluble ligand A comprises the product obtained by the reaction of alumina and the silane

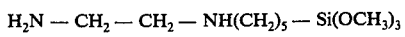

5. The catalyst as defined by claim 1, wherein the insoluble ligand A comprises the product obtained by the reaction of alumina or silica with vinyltrichlorosilane and further reacted under copolymerization conditions with a compound selected from the group consisting of vinylpyridine and acrylic acid.

6. A catalyst comprising the product obtained by the reaction of the insoluble ligand as defined by claim 2 with the coordination complex $Rh_2Cl_2(CO)_4$.

7. A catalyst comprising the product obtained by the reaction of the insoluble ligand as defined by claim 2 with the coordination complex $RhCl[P(Ph)_3]_3$.

8. A catalyst comprising the product obtained by the reaction of the insoluble ligand as defined by claim 2 with a hydrated ruthenium trichloride coordination complex.

9. A catalyst comprising the product obtained by the reaction of the insoluble ligand as defined by claim 3 with the coordination complex $Rh_2Cl_2(CO)_4$.

10. A catalyst comprising the product obtained by the reaction of the insoluble ligand as defined by claim 4 with the coordination complex $Rh_2Cl_2(CO)_4$.

11. The catalyst as defined by claim 1, wherein $M(L')_n(L'')_q$ moiety is derived from the group consisting of dichlorotetracarbonyldirhodium, tris(triphenylphosphine) chlororhodium, hydrated ruthenium trichloride, paratoluidinedicarbonylchlororhodium, tetracyclooctenedichlorodirhodium, tetrakis(triphenylphosphite) platinum, bis(benzonitrilephosphite) palladium and tripyridinetrichlororhodium.

12. A process for the preparation of the catalytically active insoluble metallic complexes as defined by claim 1 comprised of reacting a coordination complex of a Group VIII noble metal with an insoluble ligand obtained by reacting an alkoxysilane or a chlorosilane having a radical in the silane molecule selected from the group consisting of a hydrocarbyl amine and a carboxylic acid with an inorganic nucleus comprised of silica or alumina and recovering the catalyst.

13. The process as defined by claim 12, wherein the insoluble ligand is prepared by reacting a vinylalkoxysilane or vinylchlorosilane with an inorganic nucleus comprised of silica or alumina followed by the copolymerization of the resultant product with a compound selected from the group consisting of vinylpyridine and acrylic acid.

14. A process for the preparation of the catalytically active insoluble metallic complexes as defined by claim 1 comprised of reacting a first coordination complex of a Group VIII noble metal with a hydrocarbyl amine or carboxylic acid substituted chlorosilane or alkoxysilane to obtain a second coordination complex, reacting said second coordination complex with an inorganic solid substrate selected from the group consisting of silica and alumina and recovering the catalyst.

* * * * *